(12) United States Patent
Hutchinson (10) Patent No.: US 8,007,522 B2
(45) Date of Patent: Aug. 30, 2011

(54) METHODS FOR CORRECTION OF SPINAL DEFORMITIES

(75) Inventor: John Hutchinson, Rudgeway (GB)

(73) Assignee: DePuy Spine, Inc., Raynham, MA (US)

( * ) Notice: Subject to any disclaimer, the term of this patent is extended or adjusted under 35 U.S.C. 154(b) by 395 days.

(21) Appl. No.: 12/365,225

(22) Filed: Feb. 4, 2009

(65) Prior Publication Data
US 2009/0216280 A1 Aug. 27, 2009

Related U.S. Application Data (60) Provisional application No. 61/026,048, filed on Feb. 4, 2008.

(51) Int. Cl.
*A61B 17/70* (2006.01)

(52) U.S. Cl. .................................. 606/279; 606/266

(58) Field of Classification Search ............. 606/104, 606/86 A, 60, 246–279, 300, 305, 306, 319, 606/328, 331
See application file for complete search history.

(56) References Cited

U.S. PATENT DOCUMENTS

| | | | |
|---|---|---|---|
| 5,129,388 A | | 7/1992 | Vignaud |
| 5,154,719 A | | 10/1992 | Cotrel |
| 5,385,565 A | * | 1/1995 | Ray .................. 606/86 A |
| 5,443,467 A | | 8/1995 | Biedermann |
| 5,520,689 A | | 5/1996 | Schlapfer |
| 5,672,176 A | | 9/1997 | Biedermann |
| 5,989,250 A | * | 11/1999 | Wagner et al. ............ 606/250 |
| 6,113,601 A | | 9/2000 | Tatar |
| 6,224,598 B1 | | 5/2001 | Jackson |
| 6,251,112 B1 | | 6/2001 | Jackson |
| 6,258,090 B1 | | 7/2001 | Jackson |
| 6,261,287 B1 | | 7/2001 | Metz Stavenhagen |
| 6,296,642 B1 | | 10/2001 | Morrison |
| 6,355,038 B1 | | 3/2002 | Pisharodi |
| 6,361,535 B2 | | 3/2002 | Jackson |
| 6,379,356 B1 | | 4/2002 | Jackson |
| 6,440,132 B1 | | 8/2002 | Jackson |
| 6,454,768 B1 | | 9/2002 | Jackson |
| 6,454,772 B1 | | 9/2002 | Jackson |
| 6,458,132 B2 | | 10/2002 | Choi |
| 6,485,494 B1 | | 11/2002 | Haider |

(Continued)

FOREIGN PATENT DOCUMENTS

EP 470660 7/1995

(Continued)

OTHER PUBLICATIONS

Moss Miami Polyaxial Reduction Screw Surgical Technique, DePuy AcroMed, Inc. 1998.

(Continued)

*Primary Examiner* — Eduardo C Robert
*Assistant Examiner* — Lynnsy Schneider (57) ABSTRACT

A method of treating a spinal column shape deformation includes fixing at least two fixation screw assemblies to respective vertebrae, sliding a rod between the arm extensions on each of the fixation screw assemblies, swinging the channels of the screw assemblies relative to the fixation screws so that the channels become less inclined to the axes of the fixation screws, and so that the rod is located generally posteriorly of the spinal column, locking the channel against swinging relative to the screw, rotating the rod about its axis relative to at least one of the channels, and locking the rod against movement relative to the channel.

16 Claims, 7 Drawing Sheets

U.S. PATENT DOCUMENTS

| | | |
|---|---|---|
| 6,537,276 B2 | 3/2003 | Metz Stavenhagen |
| 6,540,748 B2 | 4/2003 | Lombardo |
| 6,723,100 B2 | 4/2004 | Biedermann |
| 6,726,687 B2 | 4/2004 | Jackson |
| 6,730,089 B2 | 5/2004 | Jackson |
| 6,736,820 B2 | 5/2004 | Biedermann |
| 6,740,086 B2 | 5/2004 | Richelsoph |
| 6,835,196 B2 | 12/2004 | Biedermann |
| 6,869,433 B2 | 3/2005 | Glascott |
| 6,884,244 B1 | 4/2005 | Jackson |
| 6,974,460 B2 | 12/2005 | Carbone |
| 6,997,927 B2 | 2/2006 | Jackson |
| 7,018,378 B2 | 3/2006 | Biedermann |
| 7,223,268 B2 | 5/2007 | Biedermann |
| 7,264,621 B2 | 9/2007 | Coates |
| 7,291,153 B2 | 11/2007 | Glascott |
| 7,731,736 B2 * | 6/2010 | Guenther et al. ............. 606/273 |
| 7,785,354 B2 | 8/2010 | Biedermann |
| 2002/0133159 A1 | 9/2002 | Jackson |
| 2003/0055426 A1 | 3/2003 | Carbone |
| 2003/0125741 A1 * | 7/2003 | Biedermann et al. ........... 606/61 |
| 2004/0162560 A1 | 8/2004 | Raynor |
| 2004/0186473 A1 | 9/2004 | Cournoyer |
| 2004/0186478 A1 | 9/2004 | Jackson |
| 2004/0243126 A1 * | 12/2004 | Carbone et al. ................. 606/61 |
| 2005/0080415 A1 | 4/2005 | Keyer |
| 2005/0153077 A1 | 7/2005 | Gedeon |
| 2005/0154391 A1 | 7/2005 | Doherty |
| 2005/0154393 A1 | 7/2005 | Doherty |
| 2005/0159750 A1 | 7/2005 | Doherty |
| 2005/0187548 A1 * | 8/2005 | Butler et al. .................... 606/61 |
| 2006/0084995 A1 | 4/2006 | Biedermann |
| 2006/0106383 A1 | 5/2006 | Biedermann |
| 2007/0123870 A1 | 5/2007 | Jeon et al. |
| 2007/0265621 A1 | 11/2007 | Matthis |
| 2008/0021473 A1 * | 1/2008 | Butler et al. .................... 606/63 |
| 2008/0269805 A1 * | 10/2008 | Dekutoski et al. ............. 606/279 |
| 2009/0228051 A1 | 9/2009 | Kolb |

FOREIGN PATENT DOCUMENTS

| | | |
|---|---|---|
| EP | 1295566 | 3/2003 |
| EP | 1774919 | 8/2008 |
| EP | 1795134 | 8/2008 |

OTHER PUBLICATIONS

Expedium Spine System, Dual Innie Independent Locking Technology Brochure, DePuy Spine, Aug. 1, 2004.

Viper 2 MIS Extended Tab Order Sheet, DePuy Spine, Inc., Feb. 1, 2009.

* cited by examiner

METHODS FOR CORRECTION OF SPINAL DEFORMITIES

REFERENCE TO RELATED APPLICATIONS

This application claims the benefit of U.S. Provisional patent application Ser. No. 61/026,048, entitled "Spinal Support Rod Kit", filed Feb. 4, 2008, which is incorporated herein by reference.

BACKGROUND

This invention relates to spinal support rod kits and methods for the treatment of spinal column shape deformation.

Support rods which are used to support a spinal column can be fastened to the patient's vertebrae by means of fastening devices such as for example by bone screws or hooks. The support rods can help to support the spine in a desired alignment. A support rod can define a shape towards which a deformed spine is to be corrected. Attaching the vertebrae to the rod causes vertebrae which are out of position to be drawn towards the rod, so that they can then be retained in a correct alignment against forces imposed by soft tissue tending to revert the configuration of the spine towards the deformed shape. Correction of the spinal deformation can involve application to the vertebrae of translational forces or of torsional forces or both, to cause vertebrae to translate and to twist or both.

A known system for the treatment of scoliosis involves a posterior approach using two sub-laminar hooks placed at the superior and inferior end vertebrae of the curve. A single rod is then inserted in the hooks and a distraction force is applied to correct the curve.

Subsequent refinements have reduced the forces which are applied to individual vertebrae and to improve the application of correction forces during extended periods after implantation.

More recent systems involve use of distraction and compression rods which are fixed to the spine with several hooks around the pedicles, transverse processes or laminae of some vertebrae, and/or screws through the pedicles of selected vertebrae. These multi-segmented double rod systems allow distraction and compression at different levels to improve alignment in the lateral and sagittal plane but nominal axial rotation. The Cotrel-Dubousset correction technique uses a rod rotation (rod to spine manoeuvre) in which a shaped rod is rotated in the concave side of the curve of the spine, and anchored using proximal and distal hooks. Spinal instrumentation which is sold by DePuy Spine Inc under the trade mark ISOLA uses vertebral translation (spine to rod manoeuvre) in which vertebrae are translated toward the rod with various specifically designed instruments and implants, for example hook and pedicle screw extensions and wires.

Application of torsional forces to neutral vertebrae can result in some imbalance and unwanted movement of those vertebrae.

It can be challenging during a surgical procedure to implant a spinal support rod to ensure that appropriate forces are applied to a rod in order to deform it, so that appropriate bending and torsional forces are then applied by the rod after implantation to the patient's vertebrae. Different such forces can be required at different points along the patient's spinal column. It can also be important to control the amount of force that is applied at each stage during the procedure to each vertebra because high localised forces can result in the patient's bone tissue being damaged.

SUMMARY

The present invention provides a technique for treating spinal column shape deformation in which a rod is fastened to the patient's vertebrae by means of a fixation screw assembly with a rod receiving channel with separable channel arm extensions, in which the channel can swing relative to its fixation screw through an off-centred range of angles, and a locking device which can separately lock the channel against swinging relative to the fixation screw and the rod against movement in the channel.

Accordingly, in one aspect, the invention provides a method of treating a spinal column shape deformation, which comprises:

a. fixing at least two fixation screw assemblies to respective vertebrae in which each fixation screw assembly comprises a fixation screw having a threaded shaft and a head, a channel which comprises a pair of approximately parallel arms and a base which extends between them, and an arm extension provided on each of the channel arms which is configured to be readily detached from the arm. in which:
   i. the rod can be received in the channel between the arms,
   ii. the base has a bore formed in it which is configured so that the shaft of the fixation screw but not the head thereof can extend through the bore, in which the channel can be swung through a range of angles relative to the fixation screw, at least in the plane which contains the two arms, the midpoint of the range of angles being angularly offset relative to the axis of the screw, in which the fixation step involves screwing the fixation screw into the pedicle, and orienting the channel so that it is inclined relative to the axis of its fixation screw and swung laterally relative to the spinal column, b. sliding the rod generally in the coronal plane so that it is positioned between the arm extensions on each of the fixation screws, c. swinging the channels relative to the heads of the fixation screws so that the channels become less inclined to the axes of the fixation screws, and so that the rod is located generally posteriorly of the spinal column, d. locking the channel against swinging relative to the screw, e. rotating the rod about its axis relative to at least one of the channels, and f. locking the rod against movement relative to the channel.

The method of the invention can make use of a spinal support rod kit for the treatment of spinal column shape deformations, which comprises a spinal support rod, and a fixation screw assembly comprising:

a. a fixation screw having a threaded shaft and a head, b. a channel which comprises a pair of approximately parallel arms and a base which extends between them, in which:
   i. the rod can be received in the channel between the arms,
   ii. the base has a bore formed in it which is configured so that the shaft of the fixation screw but not the head thereof can extend through the bore, in which the channel can be swung through a range of angles relative to the fixation screw, at least in the plane which contains the two arms, the midpoint of the range of angles being angularly offset relative to the axis of the screw, c. a locking device which can be fitted to the channel, and which can separately lock:
   i. the channel against swinging relative to the head of the screw, and
   ii. the rod against movement in the channel, d. an arm extension provided on each of the channel arms at a point on its arm which is further from the base of the channel the point on the arm at which the locking device is fitted to the channel, and which is configured to be readily detached from the arm.

The method of the invention has the advantage that it can facilitate loading the support rod into the channels of the fixation screw assemblies because the rod can be moved into the channels towards the spinal column approximately in the coronal plane. While the movement might not be exactly in the coronal plane (for example, the movement might be in a plane which is at an angle of up to about 30° to the coronal plane), it will be understood that this represents a different approach to techniques in which a rod is introduced into a channel on a fixation screw by movement generally in the sagittal plane. Such movement into the channels is facilitated by the fact that the channel can be swung through a range of angles relative to the fixation screw, the midpoint of the range of angles being angularly offset relative to the axis of the screw. In this way, the fixation screw can be screwed into the pedicle, generally along the posterior-anterior axis (or within 30° of that axis), and the channel can be swung so that it is open generally along the medial-lateral axis (or within 30° of that axis). The channel need only be able to swing to one side of the vertebra, which means that the channel need not swing far in the opposite direction. Accordingly, it is possible to retain sufficient material in the base of the channel to ensure that the channel can withstand loads applied to it during and after implantation.

Preferably, the angle between the midpoint of the range of angles through which the channel can be swung in the plane which contains the two arms, and the axis of the screw, is at least about 7°, more preferably at least about 10°, for example about 15° or more. The angle will generally be not more than about 30°, especially not more than about 20°.

Preferably, the range of angles through which the channel can be swung in the plane which contains the two arms is at least about 40°, more preferably at least about 45°, especially at least about 50°, for example at least about 60°. The range of angles will generally be not more than about 75°, especially not more than about 65°.

Preferably, the face of the head of the screw which contacts the bore in the base of the channel is generally rounded, especially so that it defines part of a sphere, when the screw is viewed from one side. Preferably, the face of the bore in the base of the channel which contacts the head of the screw is generally rounded when the channel is viewed from one side, and in which the angle between the axis of the bore and the axis of the channel is at least about 7°, more preferably at least about 10°, for example about 15° or more. The angle will generally be not more than about 30°, especially not more than about 20°.

The locking device can be used to retain the rod within the channel while the channel is swung relative to the head of its fixation screw so that the channel is less inclined to the axis of the fixation screw, until the rod is located generally posteriorly of the spinal column. The rod will normally be able to twist within the channel during this swinging step, so that neither the rod is locked relative to the channel nor the channel is locked against swinging relative to the fixation screw. Subsequently, the locking device can be used, in separate steps, (a) to lock the channel against swinging relative to the head of the screw, and (b) to lock the rod against movement in the channel.

Between the locking steps (a) and (b) above, the rod can be twisted relative to at least some of the channels of the fixation screw assemblies so that a torsional load is applied to the spinal column through the rod and the fixation screw assemblies.

Preferably the support rod is formed from a metallic material. This can have the advantage of permitting the support rod to be formed into a suitable shape prior to implantation, for example after or prior to an appropriate heat treatment step. Particularly preferred are titanium and certain titanium alloys. Suitable titanium based materials for use in the manufacture of spinal support rods are known.

It might be preferred in some circumstances to make use of one or more support rods which are formed from a shape memory alloy which exhibits enhanced elastic properties. Nickel-titanium based alloys are particularly suitable. Spinal support rods made from such alloys are known.

EP-A-470660 discloses apparatus for correcting the shape of a spinal column which includes a rod formed from a nickel-titanium alloy which has been treated so that it exhibits shape memory properties, in bending or in torsion or both. Articles formed from shape memory alloys can exhibit shape memory properties associated with transformations between martensite and austenite phases of the alloys. These properties include thermally induced changes in configuration in which an article is first deformed from a heat-stable configuration to a heat-unstable configuration while the alloy is in its martensite phase. Subsequent exposure to increased temperature results in a change in configuration from the heat-unstable configuration towards the original heat-stable configuration as the alloy reverts from its martensite phase to its austenite phase. The transformation from austenite to martensite on cooling begins at a temperature known as the $M_s$ temperature, and is completed at a temperature known as the $M_F$ temperature. The transformation of martensite to austenite upon heating begins at a temperature known as the $A_s$ temperature and is complete at a temperature known as the $A_f$ temperature.

A support rod which is formed from a shape memory alloy can apply corrective forces by virtue of the enhanced elastic properties that are available from such materials. Shape memory alloys can exhibit enhanced elastic properties compared with materials which do not exhibit martensite-austenite transformations and it is these properties that the present invention is concerned with in particular. The nature of superelastic transformations of shape memory alloys is discussed in "Engineering Aspects of Shape Memory Alloys", T W Duerig et al, on page 370, Butterworth-Heinemann (1990). Subject matter disclosed in that document is incorporated in this specification by this reference to the document.

Examples of shape memory alloys which might be used in the first and possibly other support rods in the kit of the invention include nickel-titanium based alloys, especially the binary alloy which contains 50.8 at-% nickel. Suitable alloys include those which satisfy ASTM F2063-00. It will often be particularly preferred for both the first and second support rods to be formed from shape memory alloys, especially for each support rod to be formed from shape memory alloys. Other metals which might be used to form support rods which do not exhibit shape memory properties include titanium and alloys thereof, for example Ti6Al4V alloys such as those which satisfy one or each of ASTM F136-02a and ASTM F1472-02a.

The support rod might be formed from a polymeric material. An example of a suitable polymeric material is an ether-ether-ketone polymer (PEEK). Polymers used for a support rod can be reinforced, for example using particulate or fibre materials. Suitable polymeric materials for use in spinal support rods are known.

The support rod will generally have a circular cross-section, at least over part of its length. This has the advantage that it can be twisted about its axis until a desired alignment is obtained, and fixed in the channel with that alignment. The method might for some applications make use of a support rod which has a non-circular cross-section at least along part of its length, which might be rounded (for example oval) or have one or more flat sides (for example square) which can facilitate locking the support rod against rotation relative to one more channels.

The transverse dimension of the support rod, which will be its diameter when circular in cross-section and the face to face distance when square, will generally be at least about 2 mm, preferably at least about 3.5 mm, more preferably at least about 5 mm, for example at least about 7 mm. The transverse dimension will generally be not more than about 10 mm.

The width of the channel between the arms will generally be such that the support rod is a sliding fit, allowing the rod to slide from the open end of the channel towards the base but with minimal play between the rod and the arms.

Preferably, each of the arm extensions is connected to its respective arm at a line of weakness which promotes separation of the arm extension from its arm. The arm extension can be separated from its arm at the line of weakness using a cutting tool. Preferably, the line of weakness is such that the arm extension can be separated from its arm by bending, possibly using a gripping tool (such as a pair of pliers) to grip the arm extension. The line of weakness should be such that the arm and its arm extension will bend preferentially at the line of weakness rather than at any other point along the length of the arm and the arm extension. The provision of such arm extensions on the arms of a rod receiving channel is known from the system which is sold by DePuy Spine Inc under the trade mark Moss Miami.

Preferably, the ratio of the length of arm extension measured from the line of weakness to the length of the channel arm measured from the base of the channel to the line of weakness is not more than about 1.0, more preferably not more than about 0.8.

The arms can have a thread on their internal faces which can be engaged by a locking device in the form of a locking screw. The use of a screw which engages a thread on the internal faces of a rod receiving channel, to retain a rod within a channel, is widely established.

Preferably, the locking device comprises a first locking screw which can engage the threads on the internal faces of the arms, and a projection which is mounted on the first locking screw which can extend beyond the rod when positioned between the first locking screw and the base of the channel, to act against the head of the fixation screw directly or indirectly. This can be used to lock the channel against swinging relative to the head of the screw. The projection can be provided as a part of a locking screw assembly, for example mounted on the screw so that the screw can rotate relative to the projection. The projection can be provided on the head of the fixation screw. The projection can be provided as a component which is separate from either or each of the locking screw and the fixation screw. A locking screw with a projection which can act against the head of a fixation screw to lock a rod engaging channel against swinging relative to the head of the fixation screw is known from the system which is sold by DePuy Spine Inc under the trade mark Expedium.

Preferably, the locking device comprises a second locking screw which can act on the rod when positioned between the second locking screw and the base of the channel to lock the rod against movement in the channel.

Preferably, the locking device comprises a first locking screw which can engage threads on the internal faces of the arms, and a projection which is mounted on the first locking screw which can extend beyond the rod when positioned between the first locking screw and the base of the channel, to act against the head of the fixation screw directly or indirectly, and a second locking screw which can act on the rod when positioned between the second locking screw and the base of the channel to lock the rod against movement in the channel, in which the first locking screw has a threaded bore extending through it in which the second locking screw can be received. A locking device which comprises inner and outer coaxial screws is known from the system which is sold by DePuy Spine Inc under the trade mark Expedium.

The support rod will often be straight in its undeformed configuration, but malleable so that it can be formed to match the natural curvature of the spine after any deformation of the spine has been corrected. It can be the case for some patients that the desired shape of the spine in the coronal plane after correction of any deformation is similar to the shape of the spine before correction of any deformation in the transverse plane. This has been relied on in the correction techniques pioneered by Cotrel, and is used in the present invention. The fixation screw assembly which is used in the invention facilitates the assembly of the rod into the channels of the fixation screws, as a result of the channels being disposed in or close to the coronal plane. A consequence of the use of the swung channels, in particular with the arm extensions, means that loads which are applied to the vertebrae when the rod is fitted into the channels can be applied progressively across several vertebrae instead of just to two adjacent vertebrae which can be the case with some existing systems.

The subsequent step of swinging the channels from the coronal plane towards the sagittal plane results in the rod being deformed from the shape which corresponds to the correct anatomical shape, and so placing the spine under a correcting force which moves the vertebrae towards the correct anatomical shape.

The use of the double function locking device in the method of the invention provides the additional advantage of enabling twisting forces to be applied to individual vertebrae before the channel is locked against movement relative to the rod. This can be achieved by applying twisting forces between the rod (which can be gripped using a tool such as a pair of pliers or grips, with appropriate jaws which are designed so as not to damage the surface of the rod) and the fixation screw channel, which can be gripped using a tool with jaws which are designed to engage the channel, for example comprising a tube which is a sliding fit over the channel. In this rotation step, the locking devices on the fixation screw assemblies along the patient's spinal column can be selectively adjusted to allow movement of the rod in the channels of one or more selected assemblies, frequently just one assembly.

The method of the invention is applicable to the correction of deformities of regions of a patient's spinal column which require correction of curvature, possible with derotation of one or more vertebrae. Accordingly, the method of the invention is particularly applicable to deformities in the thoracolumbar region of the spine.

The length of the support rod will depend on a number of factors, including the height of the patient, the length of the spinal column over which a correction is needed, and the region of the spinal column in which the correction is needed. Generally, the length of the support rod will be at least about 10 cm, preferably at least about 30 cm, for example at least about 40 cm. Its length will generally be not more than about 60 cm.

The surgeon will use his skill and judgment to determine how best to fix the support rod to the patient's spinal column. Generally, it will be fixed to the column at spaced apart vertebrae, for example at adjacent vertebrae or at every second vertebra, or at every third vertebra, or at combinations of these spacings. It will often be preferred for each connection between a support rod and the patient's vertebrae to be achieved using fixation screw assemblies in accordance with the invention. However, the method can include other fixation devices such as other screws or hooks or combinations thereof.

DETAILED DESCRIPTION

Figure 1:
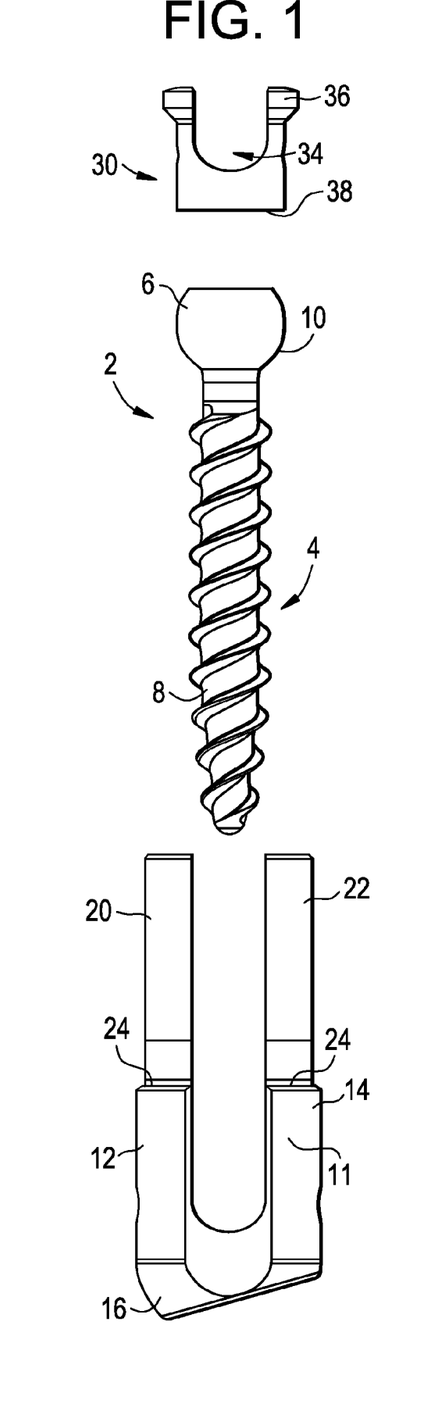
FIG. 1 is an exploded view from one side of the components of a fixation screw assembly, showing a locking device which is suitable for use in the method of the invention.
Figure 2:
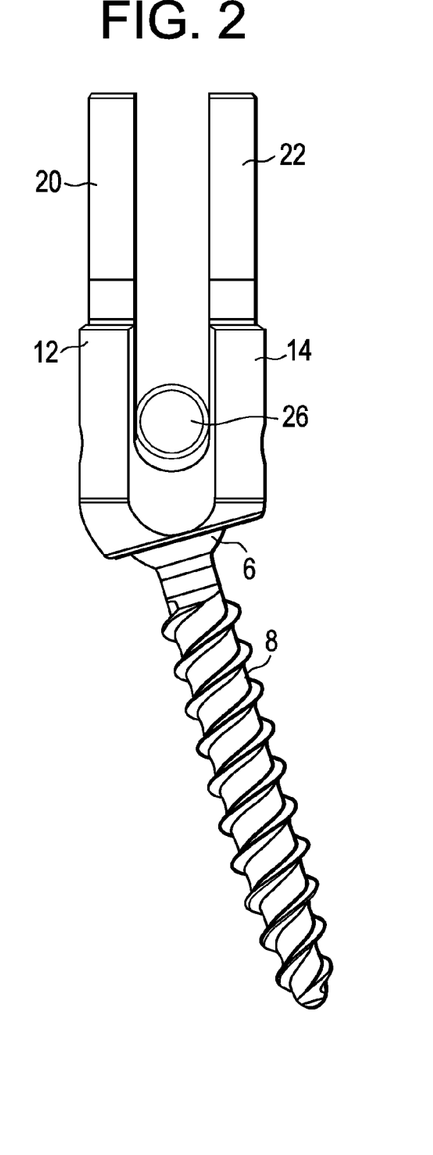
FIG. 2 is a view from one side of the fixation screw assembly shown in FIG. 1, assembled for use.

Referring to the drawings, FIGS. 1 and 2 show a fixation screw assembly 2 which can be used in the technique which is provided by the invention. The assembly comprises a fixation screw 4 which has a head 6 and a threaded shaft 8. The head 6 has a bearing surface 10 which forms part of a sphere. The head 6 has a socket formed in it which can receive the end of a driver tool to enable torsional forces to be applied to the screw to drive it into a bore in a patient's bone. It will often be preferred for the socket to have the shape of a regular polygonal, for example square or hexagonal. Other suitable sockets can be star shaped. The configuration of the thread on the shaft 8 will be selected according to the nature of the bone into which the screw assembly is to be fixed. The factors which affect the design of bone screws are well understood in the literature.

The assembly includes a channel 11 which comprises a pair of parallel arms 12, 14 and a base 16 which extends between them. The base has a bore 18 formed in it. The bore is sized so that the shaft 8 on the screw 4 can pass through it, but the head 6 cannot. The base has a socket formed in it which has the shape of part of a sphere. Accordingly, the screw can be manipulated relative to the channel when the threaded shaft of the screw extends through the bore, with the spherical surfaces of the screw head and the socket in the base in contact with one another.

The base 16 of the channel is orientated so that the angles between it and each of the arms 12, 14 of the channel, when the assembly is viewed from one side along an axis which is perpendicular to the plane which contains the two arms, are not equal. Accordingly, the angle between the bottom face of the base and a line which extends between the arms at their upper ends is non-zero. Preferably, that angle is at least about 5°. Preferably, that angle is not more than about 20°. Accordingly, the screw can be manipulated relative to the channel through a range of angles relative to the channel with the midpoint of the range being angularly offset relative to the axis of the channel (defined by the direction in which the arms extend from the base). The screw head can be locked relative against manipulation relative to the base of the channel by means of a locking device as described in more detail below.

Each of the arms 12, 14 has an arm extension 20, 22 provided on it. The arm extensions are formed integrally with their respective arms, for example by machining from a single body. A line of weakness 24 is provided where each of the arm extensions is connected to its respective arm, allowing each of the arm extensions to be separated from its respective arm.

Each arm with its respective arm extension has a thread formed on its internal surface. The threads on the opposed surfaces of the arms and the arm extensions are continuous so that a screw having a thread on its peripheral surface can engage the threads on the arms and the arm extensions, and be screwed down into the channel.

The spacing between the arms and their respective arm extensions is such that a spinal support rod 26 can be received in the channel between the arms. The rod can be formed from titanium or an alloy thereof. The rod can be locked within the channel by means of a locking device as described in more detail below.

The fixation screw assembly includes a sleeve 30. The sleeve has a circular cross-section when viewed from above and has a pair of opposed slots 34 formed in its side walls which can be aligned with the slots in the channel between the opposed arms, so that a support rod 26 extending through the channel between the arms can be accommodated within the sleeve.

The upper end 36 of the sleeve provides a flat surface through which an axial force can be applied to the sleeve to drive it axially within the channel. The sleeve is sized so that the diameter of the upper end is a sliding fit between the internal surfaces of the channel. The lower end 38 of the sleeve is shaped so that it is a close surface to surface fit against the head of the fixation screw, by virtue of matching the spherical shape of the screw head.

Figure 3:
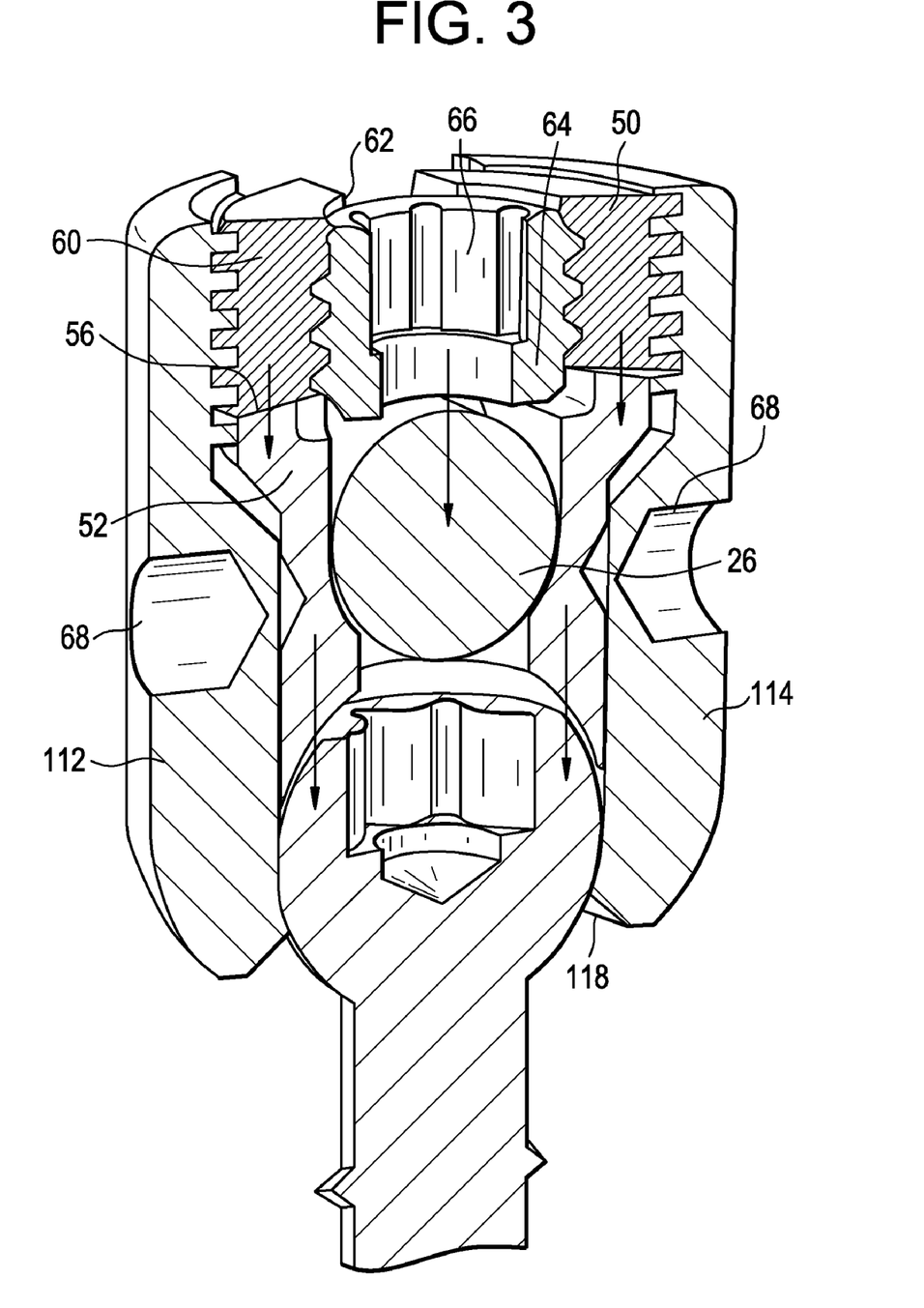
FIG. 3 is a sectional elevation through a fixation screw assembly showing in more detail a locking device which is suitable for use in the method of the invention.

FIG. 3 show a fixation screw assembly which includes a rod-receiving channel defined by two arms 112, 114 with a base (not shown because of this view being a sectional view) extending between them. The base has a bore 118 formed in it. The bore extends through a part-spherical socket which is shaped to facilitate relative manipulation between the channel and a fixation screw with a part-spherical head.

The fixation screw assembly includes a locking device which comprises a dual locking screw 50 and a sleeve 52. The sleeve has a circular cross-section when viewed from above and has a pair of opposed slots formed in its side walls which can be aligned with the slots in the channel between the opposed arms, so that a support rod 26 extending through the channel between the arms can be accommodated within the sleeve.

The upper end 56 of the sleeve provides a flat surface through which an axial force can be applied to the sleeve to drive it axially within the channel.

The lower end 58 of the sleeve is shaped so that it is a close surface to surface fit against the head of the fixation screw, by virtue of matching the spherical shape of the screw head.

The dual locking screw 50 comprises an outer screw 60 which has a bore 62 extending though it. The outer screw has a thread formed in its outer surface, which can engage with the thread which is formed on the internal surfaces of the arms 12, 14 and their respective arm extensions 20, 22. The outer screw also has a thread on the internal surface which is defined by the bore in the screw. The outer screw has a plurality of spaced apart recesses in its upper facing surface, for engaging appropriate formations on a tool by which torsional forces can be applied to the outer screw to move it within the channel.

The dual locking screw further includes an inner screw 64 which can engage the thread on the surface of the outer screw within the bore. The screw has a socket 66 which is star shaped to engage an appropriate driver with a star shaped protrusion on it.

FIG. 3 also shows a pair of opposed blind bores 68 in the outer surfaces of the channel side walls 12, 14, which can be engaged by means of a double pin gripper tool, to manipulate the channel, for example in translation or by pivoting it relative to the head of the fixation screw.

The steps that are involved in using the fixation screw assembly of FIGS. 1 and 2, with the features of the locking device which are shown in FIG. 3, include:

1. Preparing the bone to receive the fixation screw, generally by drilling a hole in the bone which is sized appropriately to receive the fixation screw.
2. Assembling the fixation screw and the channel, so that the threaded shaft of the screw extends through the bore in the base of the channel, and so that the part-spherical head of the screw is received in the part-spherical socket in the base of the channel.
3. Using a driver tool which is fitted with the fixation screw to drive the screw into the prepared hole in the bone.
4. Locating the sleeve component of the locking device within the channel, so that the slots in the side walls of the sleeve are aligned with the gaps between the channel arms, and so that the lower surface of the sleeve component is on contact with the spherical surface of the head of the fixation screw.
5. Locating a spinal support rod in the channel, so that extends from the channel through the slots in the sleeve component of the locking device and through the gaps between the arms of the channel.
6. Engaging a dual locking screw with the threads on the internal surfaces of the arms and the arms extensions of the channel.
7. Manipulating the channel using a double pin gripper tool which engages the opposed blind bores in the outer surfaces of the channel side walls, so that the channel is orientated appropriately relative to the fixation screw.
8. Applying torsional forces to the outer screw of the dual locking screw to move it within the channel using a tool which can engage the spaced apart recesses in the upper facing surface of the outer screw, so as to force the sleeve component to grip tightly the part spherical surface of the head of the fixation screw.
9. Applying torsional forces to the inner screw of the dual locking screw to move it relative to the outer locking screw so that it contacts the spinal support rod and fixes the rod relative to the channel and to the fixation screw.

Figure 4A:
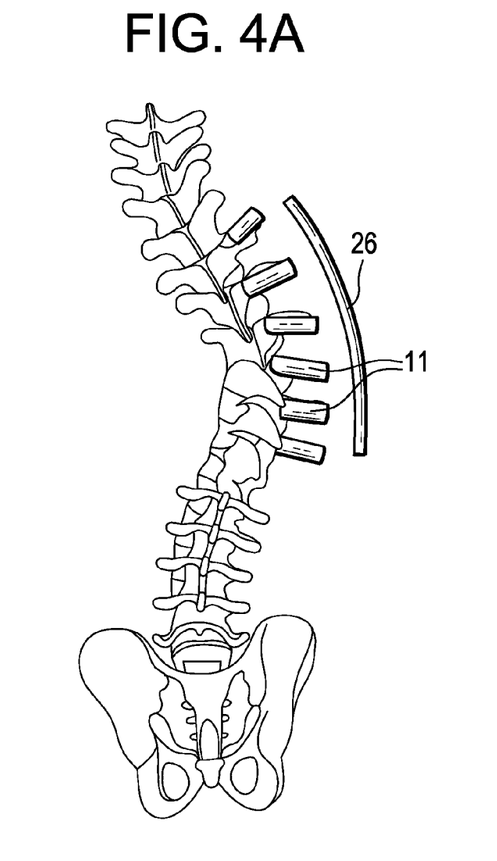
FIGS. 4a and 4b are views of a spinal column showing the location of a support rod in the channels of fixation screw assemblies which are orientated approximately in the coronal plane.
Figure 4B:
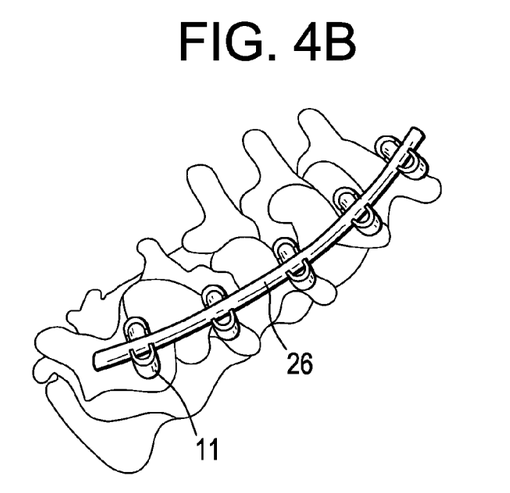
Figure 5A:
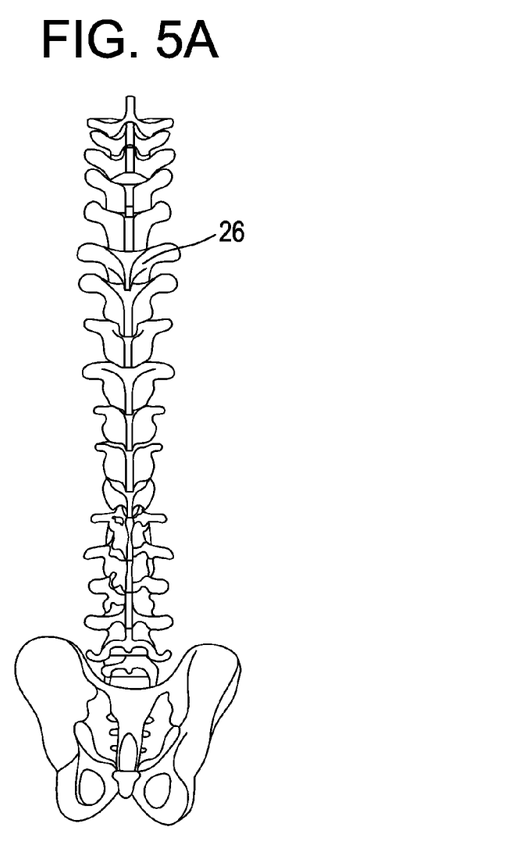
FIGS. 5a and 5b are views of a spinal column after a support rod has been located in the channels of fixation screw assemblies, and the channels have been swung from the coronal plane to the sagittal plane, to cause translation of a segment of the spinal column.
Figure 5B:
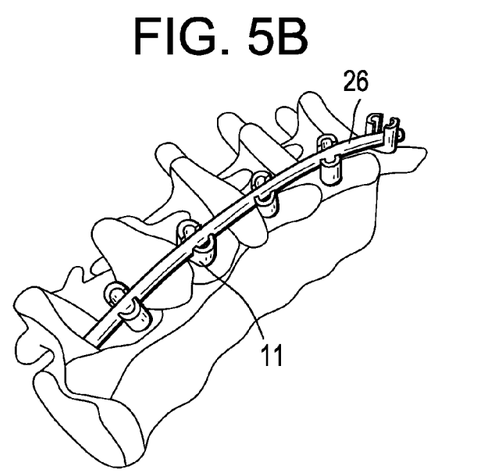
Figures 6A, 6B:
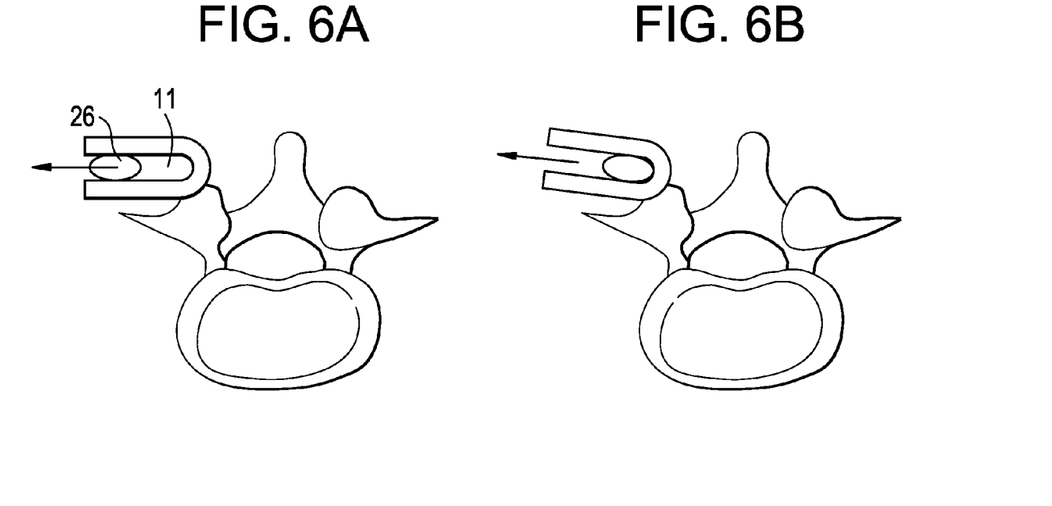
FIGS. 6a to 6d are views along the spinal column of a vertebra, a fixation screw channel and a support rod, showing schematically the translation of the vertebra caused by swinging the fixation screw channel from the coronal plane to the sagittal plane.
Figures 6C, 6D:
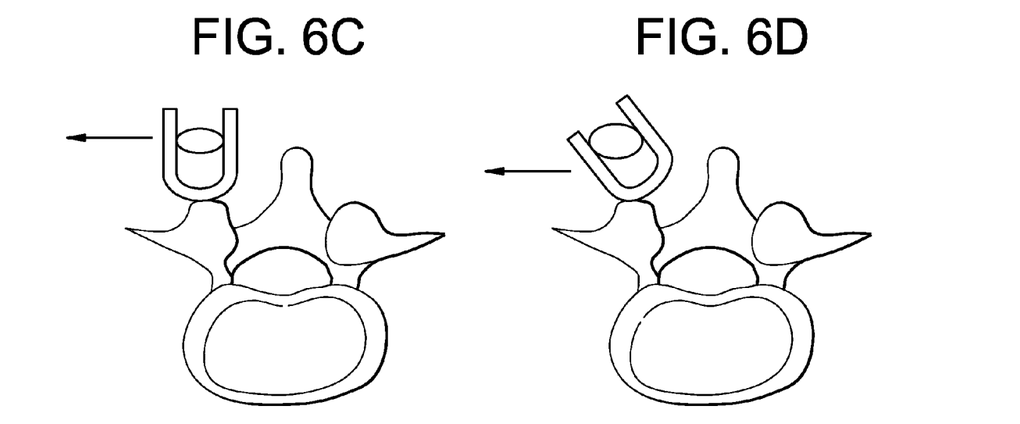
Figure 7A:
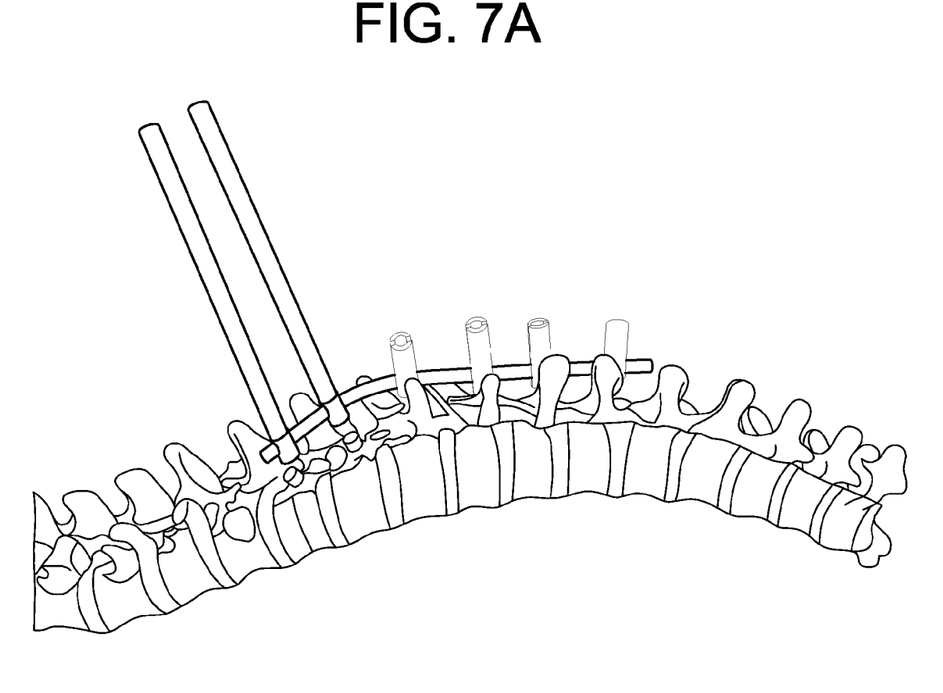
FIGS. 7a to 7d are views of a spinal column along the medial lateral axis, showing the use of a pair of tools which can engage the channels of successive fixation screw assemblies to apply a twisting force to successive adjacent vertebrae to correct misalignment.
Figure 7B:
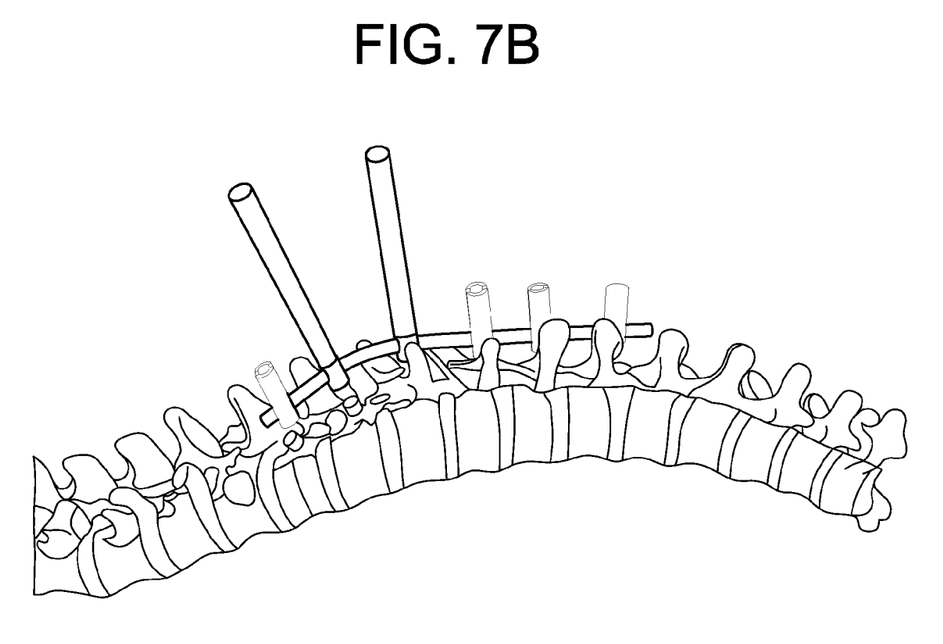
Figure 7C:
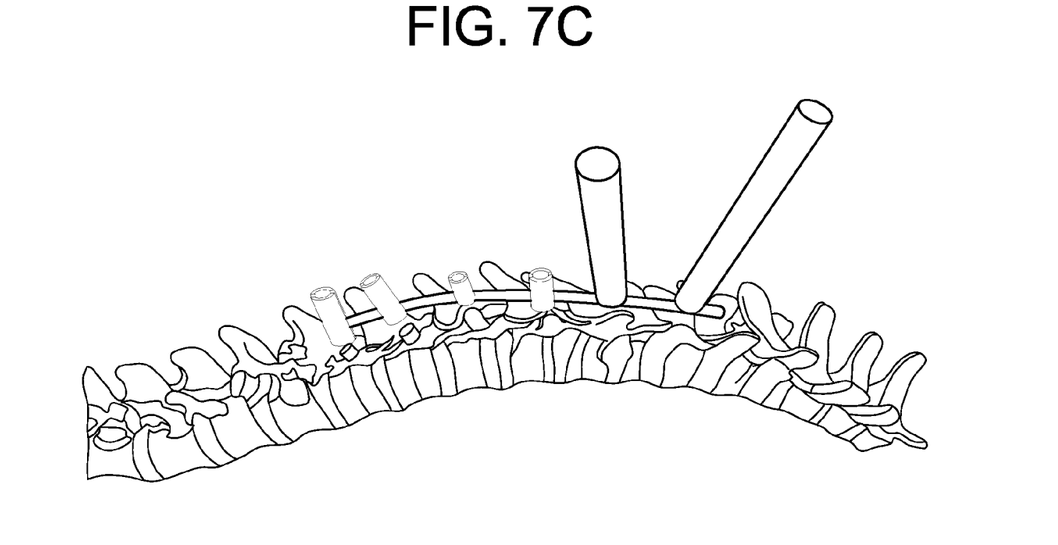
Figure 7D:
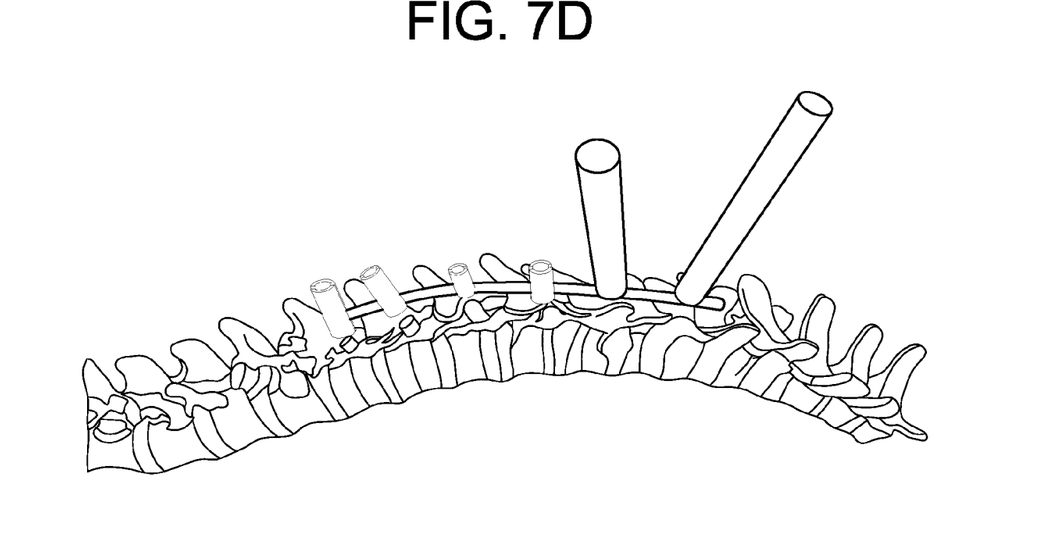

The method of the invention can be performed using a fixation screw assembly as described above. The method of the invention can involve one or more of the following steps:

1. Fixing at least two fixation screw assemblies, of the kind describe above with reference to FIGS. 1 to 3, to respective vertebrae of a spinal column of a patient requiring treatment of scoliosis, with the fixation screw oriented so that it extends into the pedicle, and so that the channel is orientated so that the arms thereof extend approximately in the coronal plane.
2. Locating a spinal support rod between the arm extensions of each of the fixation screw assemblies so that the support rod is located generally medially or generally laterally of the spinal column, in which the spinal support rod is curved along its length, so that the curvature matches (a) the shape of the deformed spine when the rod is placed alongside the spine and viewed along the anterior posterior axis, and also (b) the shape of the corrected spine when the rod is placed alongside the spine and viewed along the medial lateral axis.
3. Using dual locking screws within the channels of the fixation screw assemblies to retain the spinal support rod loosely between the arm extensions, as shown in FIGS. 4a and 4b.
4. Swinging the channels relative to the heads of the fixation screws so that the channels become closer to being aligned with the sagittal plane and the support rod becomes located generally posteriorly of the spinal column, as shown in FIGS. 5a and 5b. In this step of the method, deformation of the spinal column can be corrected by a translation of adjacent vertebrae in one or more segments of the spinal column, as shown in FIGS. 6a to 6d.
5. Using the outer screw part of each of the dual locking screws to lock each channel against movement relative to the head of its respective fixation screw.
6. Locking the rod against movement relative to selected ones of the channels, in many cases preferentially the channels which are located towards the ends of the rod, using the inner screw part of the dual locking screws.
7. Applying a twisting force to a vertebra by gripping the channels of the fixation screw assembly which is fixed to that vertebra, so that the vertebra is twisted relative to the spinal support rod, and then locking the channel against rotation relative to the rod using the inner screw part of the dual locking screw. In this step of the method, deformation of the spinal column can be corrected by rotating adjacent vertebrae in one or more segments of the spinal column. This step can be repeated as required sequentially to one or more of the vertebrae, generally successively to adjacent vertebrae along the spinal column, as shown in FIGS. 7a to 7d. The channels of the fixation screw assembly can be gripped using a tool which comprises a socket having a circular cross-section and a circular core, in which a channel can be received in the annular space between the core and the socket wall.
8. Ensuring that the rod is locked against movement relative to each channel using the inner screw part of the dual locking screws.
9. Separating the arm extensions from the arms of the channels of the fixation screw assemblies.

The use of the fixation screw assembly described above with reference to the drawings in the method and kit of the invention has the advantages that:
1. The channels of the fixation screw assemblies can be moved between a position in which the arms lie in the sagittal plane and a position in which the arms lie in the coronal plane, by virtue of the midpoint of the range of angles through which the channel can be moved relative to the fixation screw being offset.
2. The arm extensions on the channels of the fixation screw assemblies allow a spinal support rod to be located within the channels loosely without excessive deformation of the rod when first located there, especially when the channels of the fixation screw assemblies lie approximately in the coronal plane.
3. The use of a dual screw locking device allows separate locking of the channel against swinging relative to the head of the screw, and the rod against movement in the channel. This can facilitate the performance of separate steps of the method in which deformation is corrected by application of translational forces and rotational forces respectively.

The invention claimed is:

1. A method of treating a spinal column shape deformation, which comprises:
    fixing at least two fixation screw assemblies to respective vertebrae in which each fixation screw assembly comprises a fixation screw having a threaded shaft and a head, a channel which comprises a pair of approximately parallel arms and a base which extends between them, and an arm extension provided on each of the channel arms which is configured to be readily detached from the arm in which:
    the rod can be received in the channel between the arms,
    the base has a bore formed in it which is configured so that the shaft of the fixation screw but not the head thereof can extend through the bore, in which the channel can be swung through a range of angles relative to the fixation screw, at least in the plane which contains the two arms, the midpoint of the range of angles being angularly offset relative to the axis of the screw,
    in which the fixation step involves screwing the fixation screw into the pedicle, and orienting the channel so that it is inclined relative to the axis of its fixation screw and swung laterally relative to the spinal column,
    sliding the rod generally in the coronal plane so that it is positioned between the arm extensions on each of the fixation screw assemblies,
    swinging the channels relative to the heads of the fixation screws so that the channels become less inclined to the axes of the fixation screws, and so that the rod is located generally posteriorly of the spinal column,
    locking the channel against swinging relative to the screw,
    rotating the rod about its axis relative to at least one of the channels, and
    locking the rod against movement relative to the channel.

2. A method as claimed in claim 1, in which the arms have a thread on their internal faces.

3. A method as claimed in claim 2, which includes a locking device comprising a first locking screw which can engage the threads on the internal faces of the arms, and a projection which is mounted on the first locking screw which can extend beyond the rod when positioned between the first locking screw and the base of the channel, to act against the head of the fixation screw directly or indirectly.

4. A method as claimed in claim 3, in which the locking device comprises a second locking screw which can act on the rod when the rod is positioned between the second locking screw and the base of the channel to lock the rod against movement in the channel.

5. A method as claimed in claim 2, in which includes a locking device comprising a first locking screw which can engage the threads on the internal faces of the arms, and a projection which is mounted on the first locking screw which can extend beyond the rod when positioned between the first locking screw and the base of the channel, to act against the head of the fixation screw directly or indirectly, and a second locking screw which can act on the rod when the rod is positioned between the second locking screw and the base of the channel to lock the rod against movement in the channel, in which the first locking screw has a threaded bore extending through it in which the second locking screw can be received.

6. A method as claimed in claim 1, in which each of the arm extensions is connected to its respective arm at a line of weakness which promotes separation of the arm extension from its arm.

7. A method as claimed in claim 6, in which a ratio of the length of arm extension measured from the line of weakness to the length of the channel arm measured from the base of the channel to the line of weakness is not more than about 1.0.

8. A method as claimed in claim 1, in which a face of the head of the screw which contacts the bore in the base of the channel is generally rounded when the screw is viewed from one side.

9. A method as claimed in claim 1, in which a face of the bore in the base of the channel which contacts the head of the screw is generally rounded when the channel is viewed from one side, and in which the angle between the axis of the bore and the axis of the channel is at least about 10°.

10. A method as claimed in claim 1, in which the angle between the midpoint of the range of angles through which the channel can be swung in the plane which contains the two arms, and the axis of the screw, is at least about 10°.

11. A method as claimed in claim 1, in which the range of angles through which the channel can be swung in the plane which contains the two arms is at least about 60°.

12. A method of treating a spinal column shape deformation, the method comprising:
    fixing at least a first fixation screw assembly to a first vertebra, the first fixation screw assembly having a fixation screw, a channel that is adjustable relative to the fixation screw and that is defined by a pair of opposed arms, and an arm extension provided on each of the arms, the fixation screw having an axis extending from a distal tip to a proximal head,
    orienting the channel of the first fixation screw assembly to a non-zero angle relative to the axis of the fixation screw and laterally relative to the spinal column,
    sliding a rod in the coronal plane to the position the rod between the arm extensions of the first fixation screw assembly,
    adjusting the channel and thereby the rod relative to the fixation screw to reduce the angle of orientation of the channel with respect to the axis of the fixation screw,
    locking the channel relative to the fixation screw,
    rotating the rod about its axis relative to the channel, and
    locking the rod against movement relative to the channel.

13. The method of claim 12, further comprising removing the arm extensions from the arms of the channel.

14. The method of claim 12, wherein locking the channel relative to the fixation screw comprises
    connecting a locking device to the arms of the channel, and advancing the locking device into engagement with a sleeve interposed between the rod and a head of the fixation screw to press the sleeve against the head and the head against the channel.

15. The method of claim 14, wherein the locking device includes a first locking screw for engagement with internal threads provided on the arms of the channel.

16. The method of claim 15, wherein the locking device includes a second locking screw and locking the rod against movement relative to the channel comprises advancing the second locking screw into engagement with the rod to press the rod against the sleeve.

* * * * *